Figure 6:
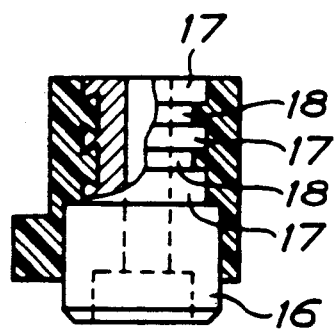

United States Patent [19]

Lundgren

[11] Patent Number: 5,064,374
[45] Date of Patent: Nov. 12, 1991

[54] ELEMENT AND METHOD FOR IMPLANT-FIXED PROSTHESIS

[75] Inventor: Dan Lundgren, Hovås, Sweden

[73] Assignee: Nobelpharma AB, Gothenburg, Sweden

[21] Appl. No.: 318,923

[22] PCT Filed: Aug. 28, 1987

[86] PCT No.: PCT/SE87/00380
§ 371 Date: Mar. 21, 1989
§ 102(e) Date: Mar. 21, 1989

[87] PCT Pub. No.: WO88/01489
PCT Pub. Date: Mar. 10, 1988

[30] Foreign Application Priority Data
Aug. 29, 1986 [SE] Sweden .................. 8603638

[51] Int. Cl.$^5$ .................. A61C 8/00
[52] U.S. Cl. .................. 433/173; 433/213
[58] Field of Search .............. 433/173, 174, 175, 176, 433/201.1, 213

[56] References Cited
U.S. PATENT DOCUMENTS

| 3,672,058 | 6/1972 | Nikoghossian | 433/174 |
|---|---|---|---|
| 3,748,739 | 7/1973 | Thibert | 433/173 |
| 4,085,506 | 4/1978 | Lew | 433/172 |
| 4,225,668 | 9/1989 | Bartoli | 433/176 |
| 4,516,937 | 5/1985 | Bosker | 433/173 |
| 4,741,698 | 5/1988 | Andrews | 433/173 |
| 4,767,328 | 8/1988 | Branemark | 433/173 |

FOREIGN PATENT DOCUMENTS

| 0111134 | 4/1986 | European Pat. Off. . |
| 8600218 | 1/1986 | PCT Int'l Appl. . |
| 416175 | 3/1981 | Sweden . |
| 448600 | 3/1987 | Sweden . |

Primary Examiner—John J. Wilson
Attorney, Agent, or Firm—Merchant & Gould, Smith, Edell, Welter & Schmidt

[57] ABSTRACT

Prefabricated construction element for an implant-fixed prosthesis, comprising a central portion (10) which can be attached to an implant-fixed anchorage element (14), and two from substantially diametrically opposite portions projecting wing-like portions (12), and the use of such construction elements for building up a unitary bridge body or a model of a bridge body by interconnecting the wing-like portions of adjacent construction elements which are mounted to implanted anchorage elements.

10 Claims, 2 Drawing Sheets

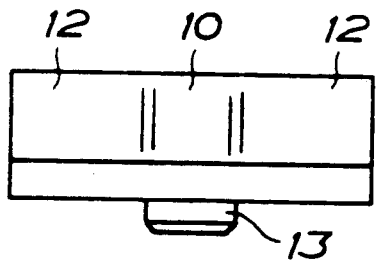
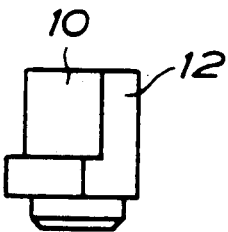
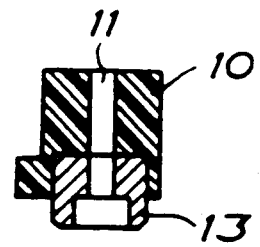
FIG. 1  FIG. 2  FIG. 4
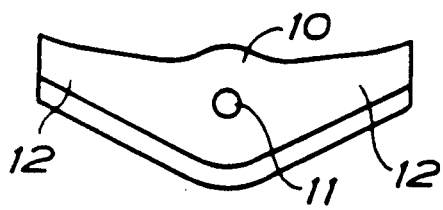
FIG. 3
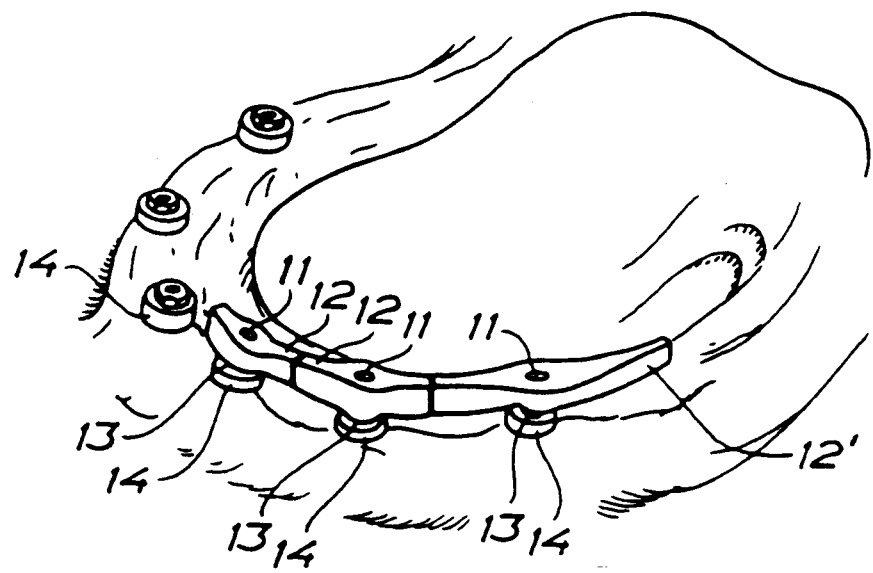
FIG. 5

ELEMENT AND METHOD FOR IMPLANT-FIXED PROSTHESIS

The invention relates to a prefabricated construction element for an implant-fixed prosthesis, i.e. a prosthesis which is partially implanted in body tissue, preferably bone tissue, the anchoring element implanted in the body tissue preferably having such properties that said element when positioned in the tissue intimately connects thereto or will be incorporated therein and with good margin can stand the loads that may be actualized without fractioning or loosing from the surrounding tissue.

It is previously known to permanently anchor e.g. tooth prosthesis (crowns, bridges, removable prosthesis) in jaw bone tissue. A method that has turned out to give a good anchorage stability and also shows a convincing documentation of permanent anchorage is the so-called osseo integration method developed by professor Per-Ingvar Brånemark and collaborators in Gothenburg. However, the construction element according to the present invention is intended for use not only with tooth prosthesis but also with prosthesis of other kinds and independently of the implantation system used. The background of the invention nevertheless will be described in connection with tooth prostheses (bridge constructions) which are implanted by applying said osseo integration method.

When applying this method an anchorage element, termed fixture, is implanted in the jaw bone. The fixture comprises a hollow titanium cylinder the outer and inner curved surfaces are provided with threads. It is positioned in such a way that the upper end surface thereof will be at the same level as the surface of the jaw bone. This first operation is followed by an unloaded healing step of critical length, during which the fixture (having the central aperture temporarily blocked by a covering screw) becomes covered by intact mucous membrane. During this healing step the bone tissue by growth will adhere to and form a unit with the implanted fixture. During a second operation the upper end surface of the fixture will be exposed and a spacer of titanium will be screwed into the center aperture thereof.

The continued procedure according to conventional technique comprises the step of securing an impression cap or impression top of steel on top of the spacer by means of a screw which is screwed into a threaded aperture in the screw by means of which the spacer has been secured to the fixture. Impression compound is applied in an impression spoon over the impression top (impression tops). When the compound has set, the impression caps fixed in the impression compound are unscrewed from the spacers. Dummies, having end surfaces of corresponding to having end surfaces of the spacers, are screwed onto the impression caps and are embedded into gypsum the impression block can then be removed by unscrewing the impression caps from the spacer dummies. The dental technician who makes the prosthesis (the bridge structure) uses the gypsum model so that the prosthesis will match the spacers screwed onto the jaw fixtures, attaches so-called no-ox-caps (of specially alloyed gold which does not oxidize) to the spacer dummies and produces a bridge body of wax (reinforced by means of a supporting plastic plate) on the no-ox-caps. This wax model of the bridge body, a so-called bite templet, is tested in the mouth of the patient with the caps being screwed onto the spacers. By this procedure it is possible not only to check the accuracy of the impression but also to determine the height of the bite and the shape of the tooth curvature. When the bite templet has been returned to the gypsum model this model is matched to a model of the opposite jaw the two models then being mounted in a so-called articulator. In the bite templet teeth of plastic material (acrylate) are attached exactly matched to the teeth of the opposite jaw. When the templet with the teeth thereof has been tested in the mouth of the patient, the tested teeth set is returned to the gypsum model in the articulator. The position of the teeth is then fixed by pre-moulding in soft plastic material allowing the teeth to be removed and then returned to exactly the same position. When the teeth have been removed a new wax which connects the no-ox-caps is carefully built up to a suitable dimension the wax body and the caps then being embedded into gypsum. The wax will be removed by melting and molten cast gold is run into the mould cavity of the gypsum the gold melting together with the no-ox-caps. The gypsum is removed from the gold bridge body which is then secured via the no-ox-caps to the spacers of the gypsum model in the articulator. The teeth are then attached to the bridge body by means of wax and a pre-moulding templet. Then a test is made in the mouth so as to check the connection of the gold bridge body to the spacers via the no-ox-caps. If the fit is acceptable the gold bridge body with the teeth retained by the wax is returned to the laboratory for replacement of the wax with plastic material (acrylate) which attaches permanently the teeth to the gold by means of a specific pressing method. The construction is now ready to be screwed onto the spacers attached to the fixtures of the jaw via the no-ox-caps moulded into the bridge body.

The procedure described is cumbersome and time consuming above all in producing the impression and testing the bite templet which is done by the dentist, and the work of the dental technician when modelling the wax model of the bridge body. The purpose of the invention is to minimize or completely eliminate some of these operations and, on the basis of work saving laboratory and clinical work steps, to rationalize and to make cheaper the production of that part of the prosthesis (the bridge construction) which is to be connected to the anchorage elements, the quality of the attachment at the same time being maintained or improved. This is made possible by the production of a wax model of the bridge body being replaced by a simpler operation which is less time consuming and moreover can be performed by the dentist directly on the spacers located in the jaw.

For said purpose the invention provides a construction element of the kind referred to above and having the characteristics appearing from claim 1.

This construction element provides in a supple manner modification of existing technique in order to reduce clinic time as well as laboratory time in the production of prostheses (bridge constructions) by using the construction element in accordance with claim 10.

Figure 7:
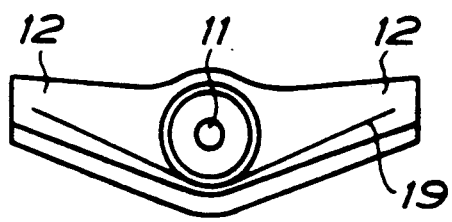
Figure 8:
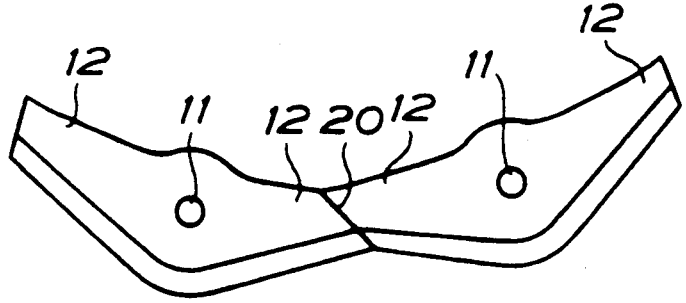
Figure 9:
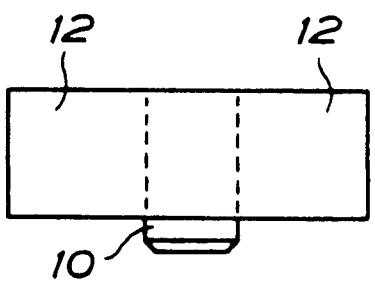
Figure 10:
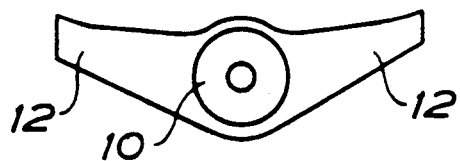

For illustration embodiments of the invention will be described in more detail below reference being made to the accompanying drawings in which FIG. 1 is a side view of a construction element according to the invention in a first embodiment thereof, FIG. 2 is an end view of the construction element, FIG. 3 is a plan view of the construction element, FIG. 4 is a central vertical sectional view of the construction element, FIG. 5 is a perspective view showing construction elements mounted on spacers in the jaw, and illustrates the build-up of a bridge body or a model of a bridge body, FIG. 6 is an enlarged vertical sectional view of another embodiment of the construction element, FIG. 7 is a horizontal sectional view of a third embodiment of the construction element, FIG. 8 is a plan view illustrating the interconnection of construction elements of FIG. 7, FIG. 9 is a side view and FIG. 10 a plan view of a fourth embodiment of the construction element.

The construction element shown in FIGS. 1 to 4 is made of a tissue compatible plastic material consisting of two components which sets preferably at room temperature to a shape-permanent body and can be evaporated without producing contaminants. A plastic material which satisfies these requirements is a plastic material which is marketed under the registered trade mark DURALAY ® and comprises a powder component, and a liquid component said two components being cold mixed for setting. The set material can be easily worked by means of cutting tools, e.g. grinding and sawing, and it can also easily be built up and glued by application of mixed plastic compound, before it has set. The construction element for consideration of strength is L-shaped in cross section and comprises a thicker central portion 10 with a through central circular aperture 11 and two projecting wing-shaped portions 12 from diametrically opposite positions of the central portion wing-shaped portions 12 which are slightly curved to harmonize with an imagined tooth curvature. In the construction element a turned no-ox-cap 13 of gold is attached to or molded into one end of the element coaxially with the aperture therein. The cap 13 projects from the construction element at the flanged edge.

In use, a construction element like that described above, is mounted on each of the spacers positioned in the jaw, shown in FIG. 5 at 14, by screwing the no-ox-caps onto the spacers by means of screws which pass through the apertures 11. When the wings have been cut and adjusted in relation to each other in a harmonic curvature by rotating the construction elements the wings can easily be built together to form a carrying bridge body directly in situ in the mouth by applying mixed plastic compound which has not set yet. Between this bridge body and the underlying mucous membrane of the jaw an impression compound such as XANTOPREN ® or IMPREGUM ® is injected and on top of the bridge body a wax index is positioned over which the patient has to bite. By this procedure the relationship of the bridge body to the underlying mucous membrane and the opposite jaw is obtained. The bridge body is unscrewed from the spacers and the no-ox-caps are secured to spacer dummies which are anchored in gypsum. On this gypsum model the bridge body then can be given the shape which it must have in order to harmonize with the jaw, and is provided with a suitable set of teeth (acryl teeth) attached to the bridge body by means of wax. The relative position of the teeth is secured by premoulding in soft plastic material. Then the teeth and wax are removed. The bridge body with the no-ox-caps is embedded in gypsum so that a bridge body of gold can be cast in the cavity formed in the gypsum after evaporation of the bridge body of plastic material. When the bridge body of plastic material is adjusted it should be made as slender as possible but sufficiently strong in order that the bridge body of gold will have the necessary strength. The bridge body can be cast as a single piece without bubbles being formed while obtaining a shape-permanent bridge body of gold. It can also be cast in several pieces which are interconnected.

According to a further development of the invention the bridge body built up in the mouth by using the construction elements is not used for forming a cavity for casting a bridge body of gold as described above; it is used to support directly actual teeth on the spacers positioned in the jaw.

In this latter embodiment the relatively expensive no-ox-cap of gold can be replaced by a considerably cheaper cap of titanium, chromium-cobalt or another suitable metal. However, the cap must be constructed such that it can be securely anchored in the plastic material of the construction element. FIG. 6 discloses such an embodiment wherein the cap is shown at 16 and forms an axial extension which has annular flanges 17 and undercut annular grooves 18 defined therebetween. The plastic material of the construction element can comprise polymethyl metacrylate or polycarbonate. In the first case the plastic material can be reinforced by means of coal fibres and in the latter case by means of glass fibres. Preferably the fibres are applied in the manner disclosed in FIG. 7 according to which the fibres 19 are extended from one wing 12 so as to pass around the central aperture over one or more turns and then extend into the other wing 12. The fibres also can be short (one millimeter or a few millimeters) and can be applied with the main direction in the longitudinal direction of the wings and circularly around the central aperture positioned such that they overlap each other. The interconnection of adjacent wings in both embodiments can be made by using methyl metacrylate which is polymerized to polymethyl metacrylate. The wings preferably are overlapped as shown in FIG. 8 at 20, and in order to optimize the strength of the joints the wings at the ends thereof can be divided into thread- or blade-like slots or form small apertures or undercuts in the surface layer. For the rest the bridge body is built up in the same manner as described above when using the construction element of FIGS. 6 to 8. When the tooth set with the teeth attached to the bridge body by means of wax or suitable plastic material has been tested the teeth are attached permanently by pressing of methyl metacrylate which is polymerized to polymethyl metacrylate.

If the construction element is made of polycarbonate, a reinforcement of coal fibres can be applied to the bridge body produced therefrom, preferably on the back side. The coal fibres applied to the outside can be baked into polymethyl metacrylate. The fibres can be laid over the joints between adjacent interconnected wings but above all they can be laid onto the longer wings 12' at the ends of the bridge body (FIG. 5) which may be exposed to a larger load than the rest of the bridge body.

For narrow bridge bodies coal fibre reinforced polymethyl metacrylate is preferred since such material gives the strongest bridge construction. The disadvantage of this material is that the bridge construction due to the presence of coal fibres will have a gray-black colour tone which is disfiguring, and therefore the bridge body must be painted at least on the front side thereof. Polycarbonate is therefore used as often as the bridge can be made as heavy as is necessary in order that the bridge shall have sufficient strength when made of this material.

In a modification of this embodiment also the cap is made of plastic material the cap being pressed, moulded or turned in the shape of a cylinder which can be secured to the spacers. The wings apertured centrally for the cap then are secured to the cap by using methyl metacrylate which is set. This embodiment is shown in FIGS. 9 and 10. The wings possibly can be mounted when the bridge body is built up in the mouth, and in that case the wings can be displaced along the cylinder and can be attached at the desired height. In a further modification of this embodiment the construction element as well as the wings thereof are pressed or cast as an integral piece.

In a third embodiment of the construction element of the invention this element as a whole is made of titanium or a suitable alloy thereof. The construction element then is made by mechanical working (turning, milling, electro-erosion) including also the cap 13. This can also be made as a separate cylindrical element and be attached to the rest of the construction element by laser welding or plasma welding in analogy with the disclosure of FIGS. 9 and 10. Alternatively the wings can be stamped as a separate element with a through aperture through which the central cylindrical element is passed and is secured by welding. The construction elements are applied in the mouth with the wings overlapping each other. When the loose components have been united by means of a suitable plastic material such as DURALAY ®, the bridge body is transferred in the manner described above to a gypsum model where exact cutting and grinding of the wings is performed in order to provide a bridge construction by adjacent wings being interconnected by laser welding or plasma welding of the abutment joints. Possibly the central cylindrical elements can be welded to the remaining construction elements at the same time as the wings are interconnected. This means that adjustment of the wings can be made also vertically by displacement of the wings along the central cylinder.

The surface of the construction elements of titanium, can be provided with undercut portions or be treated chemically for retention of the actual tooth superstructure on the bridge construction. By using titanium, which is a metal recognized as compatible with tissue, the same material is obtained in that portion of the prosthesis construction which is connected to the anchorage elements as in such elements proper. Since the price of this metal is a fraction of the price of gold a considerable saving of material cost is achieved, the prefabrication technique at the same time considerably reducing the labour costs.

In a modification of the latter embodiment the cylindrical element of titanium can form part of a construction element the rest of which comprises a plastic material, e.g. DURALAY ®. In this case the bridge body built up in the mouth comprises a model which is then removed from the cylindrical elements (titanium caps) 13 and is copied in titanium in a copying mill the copy then being connected to the caps 13 by laser welding. This embodiment principally can be in accordance with FIGS. 9 and 10, and in that case the element forming the wings 12 is of a plastic material and the central portion 10 is a separate cylinder of titanium which is not, however, connected to the wings, these can be rotated and displaced vertically on the cylinder. As a consequence thereof the wings can be adjusted in the manner previously described and can be temporarily locked in the adjusted position to the cylinder by the application of plastic material in connection with the upper portion of the cylinder. The interconnected wing system can be lifted from the cylinders and a titanium copy thereof can be made in a copying mill. The titanium copy then is applied to the titanium cylinders and is connected therewith by laser welding.

The invention has been described with reference to tooth prostheses but can be applied also to prostheses of other types e.g. ear and nose prostheses, which are connected to anchorage elements implanted in bone tissue.

I claim:

1. Prefabricated construction element for an implant-fixed prosthesis comprising a central portion to be attached to an implant-fixed anchorage element, and to two wing-like portions integral with said central portion projection from substantially diametrically opposite positions of the central portion, each of said wing-like portions terminating at a free end to be connected to the free end of a wing of an adjacent prefabricated construction element.

2. Construction element as in claim 1 wherein a cap matching the anchorage element is attached to the central portion.

3. Construction element as in claim 2 wherein the element excepting the cap comprises a plastic material.

4. Construction element as in claim 3 wherein the plastic material comprises a fibre reinforced plastic material.

5. Construction element as in claim 1 wherein the central portion is shaped to match directly the anchorage element.

6. Construction element as in claim 5 wherein the construction element in its entirety consists of a plastic material.

7. Construction element as in claim 5 wherein the central portion consists of a metal compatible with tissue, and wherein the wings consist of a plastic material.

8. Construction element as in claim 1 wherein the element in its entirety consists of a metal compatible with tissue.

9. Implant-fixed prothesis including a plurality of prefabricated construction elements, each construction element including a central portion to be attached to an implant-fixed anchorage element, and two wing-like portions integral with said central portion projecting from substantially diametrically opposite positions of the central portion, each of said wing-like portions terminating at a free end to be connected to the free end of a wing of an adjacent prefabricated construction element; wherein adjacent wings of the construction elements when mounted to the implanted anchorage elements are matched to each other and are interconnected to a unitary bridge body.

10. Prefabricated construction element for an implant-fixed prosthesis comprising a central portion to be attached to an implant-fixed anchorage element, and two wing-like portions projecting from substantially diametrically opposite positions of the central portion, each of said wing-like portions terminating at a free end to be connected to the free end of a wing of an adjacent prefabricated construction element, and said wings including a separate element which is rotatably and displaceably connected to the central portion.

* * * * *

UNITED STATES PATENT AND TRADEMARK OFFICE
CERTIFICATE OF CORRECTION

PATENT NO. : 5,064,374

DATED : 12 November 1991

INVENTOR(S) : Lundgren

It is certified that error appears in the above-identified patent and that said Letters Patent is hereby corrected as shown below:

Column 6, claim 1, line 3 delete the word "to" after "and".

Column 6, claim 1, line 5 delete "projection" and insert --projecting--.

Signed and Sealed this

Tenth Day of August, 1993

Attest:

MICHAEL K. KIRK

Attesting Officer

Acting Commissioner of Patents and Trademarks